(12) United States Patent
Griffith

(10) Patent No.: US 6,719,951 B1
(45) Date of Patent: Apr. 13, 2004

(54) SPECIMEN COLLECTION ASSEMBLY

(76) Inventor: Sharyl A. Griffith, 319 W. Singleton Apt. #5, Centralia, MO (US) 65240

(*) Notice: Subject to any disclaimer, the term of this patent is extended or adjusted under 35 U.S.C. 154(b) by 34 days.

(21) Appl. No.: 10/086,803

(22) Filed: Mar. 1, 2002

(51) Int. Cl.[7] .................................................. B01L 3/00
(52) U.S. Cl. ...................... 422/102; 422/104; 220/755; 220/756; 220/759; 220/769; 600/573; 215/396; D24/122
(58) Field of Search ............................... 422/102, 104, 422/99; 206/217, 438, 569; 220/737, 738, 752, 754, 755, 756, 757, 758, 759, 762, 763, 764, 766, 767, 770, 769; 600/573, 574, 580; 215/395, 396, 398; 294/30, 27.1, 31.2; D24/128, 227, 122

(56) References Cited

U.S. PATENT DOCUMENTS

| 945,659 | A | * | 1/1910 | Wilson ........................ 220/759 |
| 1,066,923 | A | * | 7/1913 | Kuekes ........................ 220/759 |
| 1,271,530 | A | * | 7/1918 | Cerpial ........................ 220/759 |
| 1,423,406 | A | * | 7/1922 | Donley ........................ 220/759 |
| 1,635,119 | A | * | 7/1927 | Dziuba et al. ............... 220/759 |
| 2,059,098 | A | * | 10/1936 | Goodrum .................... 220/761 |
| 2,494,159 | A | * | 1/1950 | Bernstein .................... 220/759 |
| 3,073,493 | A | * | 1/1963 | Pfaffenberger .............. 294/154 |
| 4,244,920 | A | | 1/1981 | Manschot et al. |
| D306,648 | S | * | 3/1990 | Jones et al. ................. D24/128 |
| 5,147,342 | A | | 9/1992 | Kane et al. |
| 5,174,965 | A | | 12/1992 | Jones et al. |
| D335,180 | S | * | 4/1993 | Jones et al. ................. D24/128 |
| 5,202,094 | A | * | 4/1993 | Jones et al. ................. 422/102 |
| D338,064 | S | | 8/1993 | Jones et al. |
| D357,066 | S | | 4/1995 | Jones et al. |
| 5,409,473 | A | * | 4/1995 | Rosenshein ................. 604/329 |
| 5,422,076 | A | * | 6/1995 | Jones ......................... 422/102 |
| 5,505,331 | A | * | 4/1996 | Rathbun ..................... 220/764 |
| 5,558,840 | A | | 9/1996 | Jones et al. |
| D379,655 | S | * | 6/1997 | Savignac .................... D24/122 |
| 6,013,230 | A | * | 1/2000 | Kuchar ....................... 422/104 |
| D449,685 | S | * | 10/2001 | Morrison ................... D24/128 |
| 6,485,438 | B1 | * | 11/2002 | Minue ........................ 600/573 |
| 6,485,691 | B1 | * | 11/2002 | Jones ......................... 422/102 |
| 2002/0169395 | A1 | * | 11/2002 | Huang ........................ 600/574 |

* cited by examiner

Primary Examiner—Maureen M. Wallenhorst

(57) ABSTRACT

A specimen collection assembly for more easily and sanitarily collecting a urine sample. The specimen collection assembly includes a cup member for collecting the urine specimen. An elongated handle member coupled to the cup member for holding by a user to support the cup member in an appropriate position for collection of the urine sample.

6 Claims, 3 Drawing Sheets

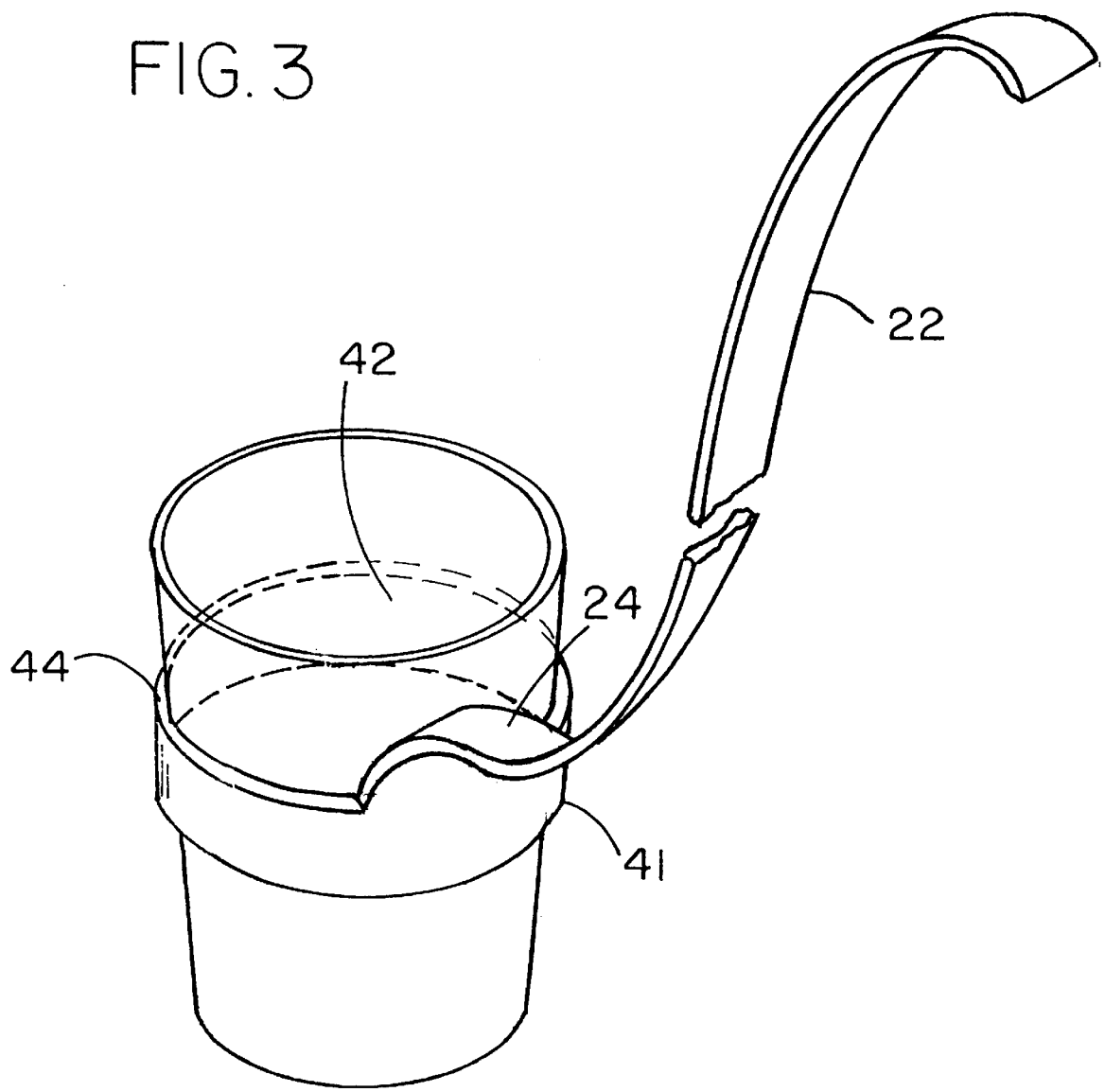

SPECIMEN COLLECTION ASSEMBLY

BACKGROUND OF THE INVENTION

1. Field of the Invention

The present invention relates to specimen collection devices and more particularly pertains to a new specimen collection assembly for more easily and sanitarily collecting a specimen, such as urine.

2. Description of the Prior Art

The use of specimen collection devices is known in the prior art. More specifically, specimen collection devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,558,840; 5,174,965; 5,147,342; 4,224,920; 338,064; and Des. 357,066.

While these devices fulfill their respective, particular objectives and requirements, the aforementioned patents do not disclose a new specimen collection assembly. The inventive device includes a cup member for collecting the urine specimen. An elongated handle member coupled to the cup member for holding by a user to support the cup member in an appropriate position for collection of the urine sample.

In these respects, the specimen collection assembly according to the present invention substantially departs from the conventional concepts and designs of the prior art, and in so doing provides an apparatus primarily developed for the purpose of more easily and sanitarily collecting a specimen such as urine.

SUMMARY OF THE INVENTION

In view of the foregoing disadvantages inherent in the known types of specimen collection devices now present in the prior art, the present invention provides a new specimen collection assembly construction wherein the same can be utilized for more easily and sanitarily collecting specimen such as urine.

The general purpose of the present invention, which will be described subsequently in greater detail, is to provide a new specimen collection assembly apparatus and method which has many of the advantages of the specimen collection devices mentioned heretofore and many novel features that result in a new specimen collection assembly which is not anticipated, rendered obvious, suggested, or even implied by any of the prior art specimen collection devices, either alone or in any combination thereof.

To attain this, the present invention generally comprises specimen collection devices.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new specimen collection assembly apparatus and method which has many of the advantages of the specimen collection devices mentioned heretofore and many novel features that result in a new specimen collection assembly which is not anticipated, rendered obvious, suggested, or even implied by any of the prior art specimen collection devices, either alone or in any combination thereof.

It is another object of the present invention to provide a new specimen collection assembly which may be easily and efficiently manufactured and marketed.

It is a further object of the present invention to provide a new specimen collection assembly which is of a durable and reliable construction.

An even further object of the present invention is to provide a new specimen collection assembly which is susceptible of a low cost of manufacture with regard to both materials and labor, and which accordingly is then susceptible of low prices of sale to the consuming public, thereby making such specimen collection assembly economically available to the buying public.

Still yet another object of the present invention is to provide a new specimen collection assembly which provides in the apparatuses and methods of the prior art some of the advantages thereof, while simultaneously overcoming some of the disadvantages normally associated therewith.

Still another object of the present invention is to provide a new specimen collection assembly for more easily and sanitarily collecting a specimen such as urine.

Yet another object of the present invention is to provide a new specimen collection assembly which includes a cup member for collecting the urine specimen. An elongated handle member coupled to the cup member for holding by a user to support the cup member in an appropriate position for collection of the urine sample.

Still yet another object of the present invention is to provide a new specimen collection assembly that reduces the possibility of the specimen cup from falling and spilling the specimen.

Even still another object of the present invention is to provide a new specimen collection assembly that allows pregnant women to more easily obtain a urine sample. The present invention allows a pregnant women, who may have trouble bending over, to more easily obtain a urine sample by using the elongated handle member to properly position the cup member.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic perspective view of the present invention showing a cup member being removably insertable into an annular member attached to an end of the handle member.

DESCRIPTION OF THE PREFERRED EMBODIMENT

Figure 1:
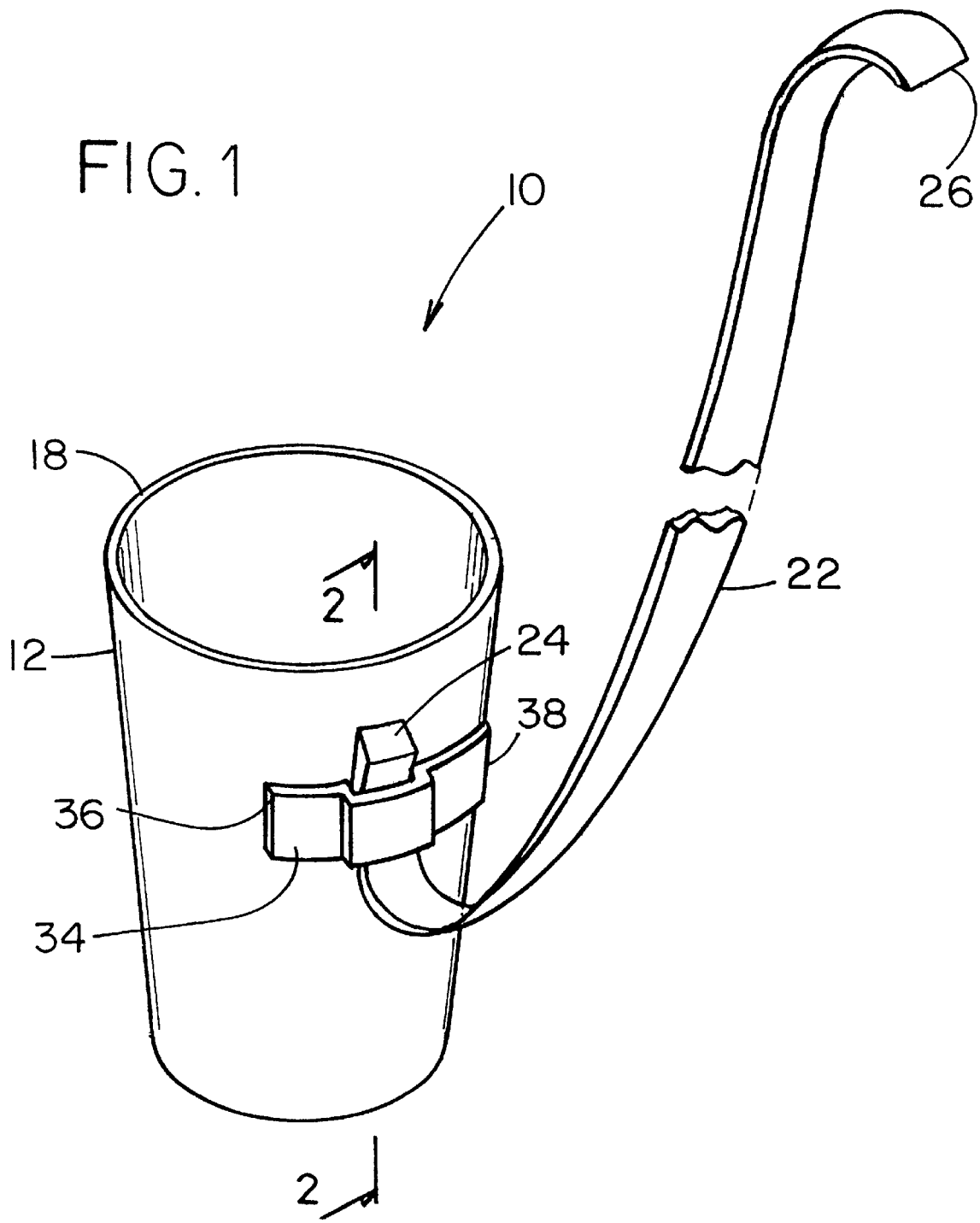
FIG. 1 is a schematic perspective view of a new specimen collection assembly according to the present invention showing a handle member attached to a cup member.
Figure 2:
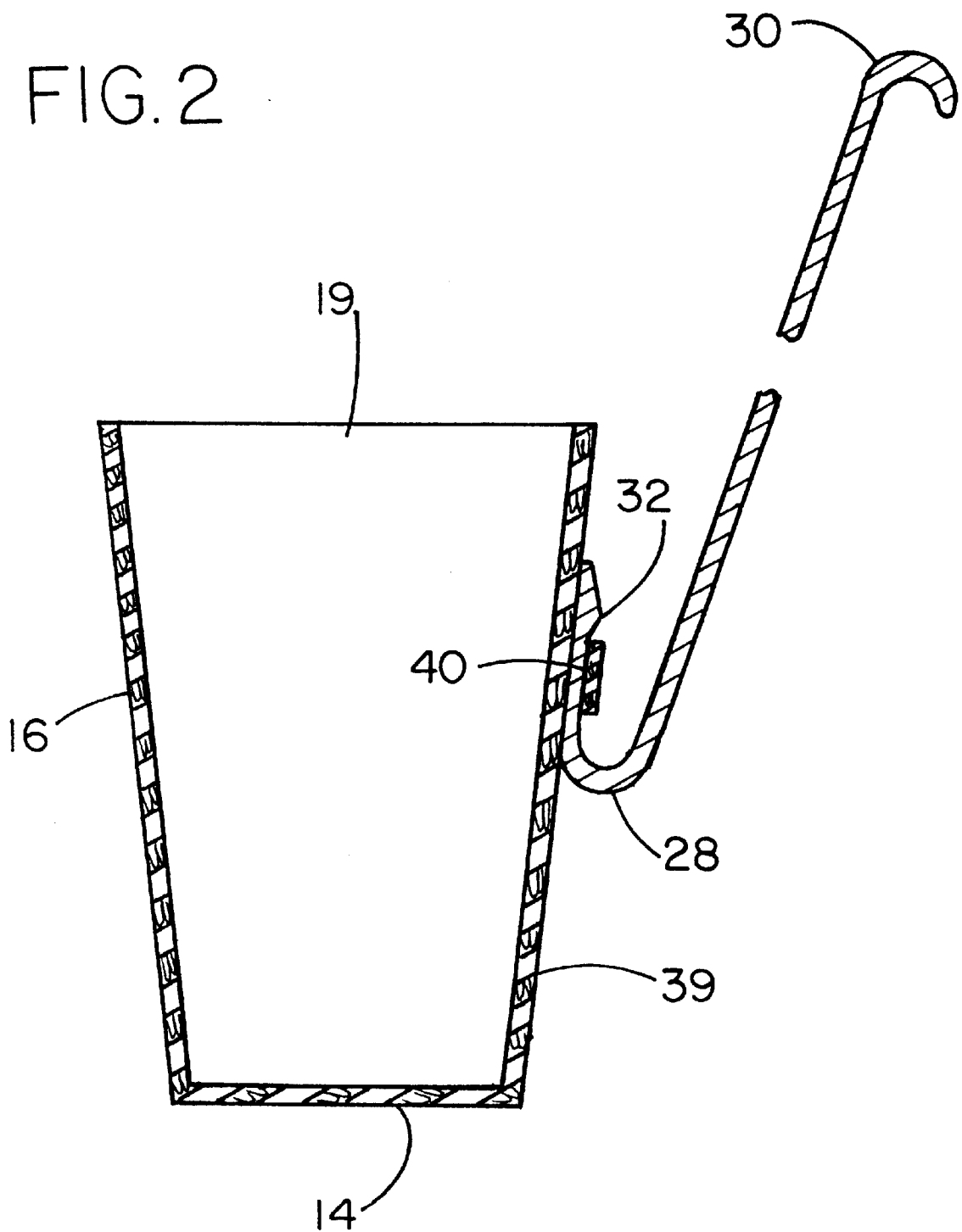
FIG. 2 is a schematic cross-sectional view of the present invention taken along the line 2—2 of FIG. 1.

With reference now to the drawings, and in particular to FIGS. 1 through 3 thereof, a new specimen collection assembly embodying the principles and concepts of the present invention and generally designated by the reference numeral 10 will be described.

As best illustrated in FIGS. 1 through 3, the specimen collection assembly 10 generally comprises a cup member 12 for collecting the urine specimen. The cup member 12 includes a bottom wall 14 and a peripheral wall 16 coupled to and extending upwardly from the bottom wall 14. An upper edge 18 of the peripheral wall 16 of the cup member 12 defines an open top 19. The cup member 12 may comprise a substantially rigid material such as, for example, a metal or a plastic material.

An elongated handle member 22 is provided for holding by a user to support the cup member 12 in an appropriate position for collection of the urine sample. The handle member 22 includes a first end 24 and a second end 26. The handle member 22 may include a first bend 28 therein that is positioned generally nearer the first end 24 than the second end 26 of the handle member 22. The handle member 22 may also include a second bend 30 therein positioned generally adjacent to the second end 26 of the handle member 22. A protrusion 32 is attached to and extends away from the handle member 22. The protrusion 32 is located generally between the first end 24 and the first bend 28 of the handle member 22. The handle member 22 may comprise a substantially rigid material such as, for example, a metal or a plastic material. The handle member 22 may have a length measuring approximately sixteen inches from the first end 24 to the second end 26 of the handle member 22.

A fastening means is provided for fastening the handle member 22 to the cup member 12. The fastening means may comprise a strip 34 that includes a first end 36 and a second end 38. Each of the ends 36 and 38 of the strip 34 is attached to an outer surface 39 of the peripheral wall 16 of the cup member 12. The strip 34 forms a channel 40 between the strip 34 and the peripheral wall 16 of the cup member 12. The first end 24 of the handle member 22 is insertable through the channel 40 such that the strip 34 is positioned generally between the protrusion 32 and the first bend 28 of the handle member 22 to mount the handle member 22 to the cup member 12. The fastening means is positioned generally nearer to the open top 19 than the bottom wall 14 of the cup member 12.

In one embodiment, the fastening means may be attached to the first end 24 of the handle member 22 and the cup member 12 being removably couplable to the fastening means. The fastening means may comprise an annular member 41 having an inner surface 42. The first end 24 of the handle member 22 is attached to a top edge 44 of the annular member 41. The bottom wall 14 of the cup member 12 is removably insertable through the annular member 41 such that the outer surface 39 of the peripheral wall 16 of the cup member 12 selectively abuts the inner surface 42 of the annular member 41.

In use, a user holds the second end 26 of the handle member 22 and positions the cup member 12 in an appropriate position to obtain the urine sample.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, failing within the scope of the invention.

I claim:

1. A specimen collection assembly for collecting a urine specimen, said specimen collection assembly comprising:
   a cup member for collecting the urine specimen;
   an elongated handle member being coupled to said cup member for holding by a user to support said cup member in an appropriate position for collection of the urine sample;
   wherein said handle member has a first bend therein being positioned generally nearer a first end than a second end of said handle member, said handle member having a second bend therein being positioned generally adjacent to said second end of said handle member wherein said first end of said handle member has a strip formed thereon, said strip being attached to an outer surface of said cup member for fastening said handle member to said cup member, and
   said second bend of said handle member being substantially U-shaped such that said second end of said handle member extends back along said handle member, said second bend of said handle member being adapted for extending over a finger of a user to provide stabilization for said cup member when said cup member is used for collecting the urine specimen.

2. The specimen collection assembly of claim 1, wherein said cup member has a bottom wall and a peripheral wall coupled to and extending upwardly from said bottom wall, an upper edge of said peripheral wall of said cup member defining an open top.

3. The specimen, collection assembly of claim 2, wherein a said strip includes a first end and a second end, each of said ends of said strip being attached to an outer surface of said peripheral wall of said cup member, said strip forming a channel between said strip and said peripheral wall of said cup member, said first end of said handle member being insertable through said channel.

4. The specimen collection assembly of claim 3, additionally comprising a protrusion formed on and extending away from said handle member for securing said cup member to said handle member.

5. The specimen collection assembly of claim 4, wherein said protrusion is positioned between said first end of said handle member and said first bend of said handle member.

6. A specimen collection assembly for collecting a urine specimen, said specimen collection assembly comprising:

a cup member for collecting the urine specimen, said cup member having a bottom wall and a peripheral wall coupled to and extending upwardly from said bottom wall, an upper edge of said peripheral wall of said cup member defining an open top, said cup member comprising a substantially rigid material;

an elongated handle member for holding by a user to support said cup member in an appropriate position for collection of the urine sample, said handle member having a first end and a second end, said handle member having a first bend therein being positioned generally nearer said first end than said second end of said handle member, said handle member having a second bend therein being positioned generally adjacent to said second end of said handle member, a protrusion being attached to and extending away from said handle member, said protrusion being located generally between said first end and said first bend of said handle member, said handle member comprising a substantially rigid material, said second bend of said handle member being substantially U-shaped such that said second end of said handle member extends back along said handle member said second bend of said handle member being adapted for extending over a finger of a user to provide stabilization for said cup member when said cup member is used for collecting the urine specimen; and a fastening means for fastening said handle member to said cup member, said fastening means comprising a strip having a first end and a second end, each of said ends of said strip being attached to an outer surface of said peripheral wall of said cup member, said strip forming a channel between said strip and said peripheral wall of said cup member, said first end of said handle member with said protrusion being insertable through said channel such that said strip is positioned generally between said protrusion and said first bend of said elongated handle member to mount said handle member to said cup member, said fastening means being positioned generally nearer to said open top than said bottom wall of said cup member.

\* \* \* \* \*